(12) United States Patent
Kim et al.

(10) Patent No.: US 10,583,452 B2
(45) Date of Patent: Mar. 10, 2020

(54) METHOD FOR COATING THIN FILM IN ROLLING MANNER AND APPARATUS FOR COATING THIN FILM BY USING THE SAME

(71) Applicant: Korea Advanced Institute of Science And Technology, Daejeon (KR)

(72) Inventors: Taek-Soo Kim, Daejeon (KR); Sumin Kang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 289 days.

(21) Appl. No.: 15/480,863

(22) Filed: Apr. 6, 2017

(65) Prior Publication Data

US 2018/0078966 A1    Mar. 22, 2018

(30) Foreign Application Priority Data

Sep. 22, 2016   (KR) .......................... 10-2016-0121417

(51) Int. Cl.

| B05C 1/08 | (2006.01) |
|---|---|
| C23C 16/06 | (2006.01) |
| C23C 14/00 | (2006.01) |
| C23C 14/14 | (2006.01) |
| B05C 1/02 | (2006.01) |
| B05D 1/28 | (2006.01) |
| C23C 14/02 | (2006.01) |
| C23C 14/08 | (2006.01) |
| C23C 16/01 | (2006.01) |
| C23C 22/13 | (2006.01) |

(Continued)

(52) U.S. Cl.
CPC ............ *B05C 1/0808* (2013.01); *B05C 1/022* (2013.01); *B05D 1/283* (2013.01); *C23C 14/0005* (2013.01); *C23C 14/021* (2013.01); *C23C 14/025* (2013.01); *C23C 14/087* (2013.01); *C23C 14/14* (2013.01); *C23C 16/01* (2013.01); *C23C 16/06* (2013.01); *C23C 22/13* (2013.01); *A61F 2210/0076* (2013.01); *B05D 1/20* (2013.01); *B05D 1/286* (2013.01); *B05D 1/60* (2013.01)

(58) Field of Classification Search
CPC ............ A61F 2210/0076; B05C 1/022; B05C 1/0808; B05D 1/20; B05D 1/283; B05D 1/286; B05D 1/60; C23C 14/0005; C23C 14/021; C23C 14/025; C23C 14/087; C23C 14/14; C23C 16/01; C23C 16/06; C23C 22/13
USPC ............................ 216/37, 38, 39, 40, 90, 91
See application file for complete search history.

(56) References Cited

U.S. PATENT DOCUMENTS

| 8,878,157 | B2 * | 11/2014 | Wu .................. H01L 21/02376 257/9 |
| 2012/0318772 | A1 * | 12/2012 | Minoura ................ C25D 11/12 216/52 |

(Continued)

*Primary Examiner* — Lan Vinh
(74) *Attorney, Agent, or Firm* — Foley & Lardner LLP

(57) ABSTRACT

A method for coating a thin film in a rolling manner and a thin film coating apparatus are provided. The method includes: floating a thin film material on a liquefied material; rolling a cylindrical substrate after contacting the cylindrical substrate with the thin film material; and coating the thin film material on a surface of the cylindrical substrate by using an attraction force between the surface of the cylindrical substrate and the thin film material.

8 Claims, 16 Drawing Sheets

(51) Int. Cl.
*B05D 1/20* (2006.01)
*B05D 1/00* (2006.01)

(56) References Cited

U.S. PATENT DOCUMENTS

2013/0143156 A1* 6/2013 Mitsumori ........... G03G 9/0819
 430/123.41
2013/0269554 A1* 10/2013 Shigeta ................ B41N 1/06
 101/141

* cited by examiner

METHOD FOR COATING THIN FILM IN ROLLING MANNER AND APPARATUS FOR COATING THIN FILM BY USING THE SAME

BACKGROUND

Field

The present disclosure relates to a method for coating a thin film in a rolling manner and a thin film coating apparatus and more particularly to a method for coating by transferring a thin film material floating on a liquefied material to a cylindrical substrate or tubular substrate.

Description of the Related Art

Recently, in the field of technology of electronic devices, active research is being devoted to a wearable device, a flexible device, a stretchable device, a biomedical electronic device, etc. Accordingly, in the future, a 2-dimensional material and a thin film are absolutely necessary for the manufacture of the electronic device.

A process of depositing a thin film is required to manufacture a thin display or electronic devices. Here, chemical vapor deposition (CVD), physical vapor deposition (PVD), electroplating, Sol-Gel, etc., are used for the purpose of depositing a thin film. Also, in addition to the process of depositing a thin film, an existing method for transferring a deposited thin film to another substrate is being widely used.

Currently, regarding the thin film deposition method such as CVD, PVD, etc., or the transfer method, a planar substrate must be used due to the characteristics of the process. CVD, PVD, etc., during the thin film deposition process is performed by causing a vapor phase raw material to be phase-transited to a target substrate on which a thin film is intended to be grown and by depositing, or is performed by a method for performing a chemical bond. However, since this process requires a high temperature process, it is difficult to directly deposit a material on a substrate vulnerable to heat, such as polymer, etc. Furthermore, a substrate which is not planar makes it difficult to precisely deposit and costs a lot for the process.

A deposition method which is not affected greatly by the shape of the substrate includes the electroplating and Sol-Gel method. Regarding the electroplating, when the substrate is made of a non-conductive material such as polymer, ceramic, etc., the electroplating is almost impossible. Further, it is difficult to control the thickness of the deposited material, and the surface of the substrate is relatively rough. Also, the Sol-Gel method uses a solution harmful to the human body, and it is difficult to control the thickness of the deposited material. Further, there is a limit to the material which can be used to perform a Sol-Gel coating due to the characteristics of the process.

At present, there is no method for depositing or transferring a high quality thin film on or to not only the planar substrate but also other shaped substrates such as a cylindrical substrate or tubular substrate, etc., while controlling a fine thickness of the material.

SUMMARY

One embodiment is a method for coating a thin film in a rolling manner. The method includes: floating a thin film material on a liquefied material; rolling a cylindrical substrate after contacting the cylindrical substrate with the thin film material; and coating the thin film material on a surface of the cylindrical substrate by using an attraction force between the surface of the cylindrical substrate and the thin film material.

The method further includes removing, before the floating, a sacrificial layer after depositing the thin film material on the sacrificial layer. Therefore, a very thin film material can float on the liquefied material.

The sacrificial layer includes at least one of Cu and Ni. Therefore, the sacrificial layer can be relatively easily removed.

In the removing, the sacrificial layer is removed by using an etchant. A thin film material that a user wants can easily float on the liquefied material.

The attraction force is greater than an adhesive force between the liquefied material and the thin film material. Therefore, the thin film material can be coated on the surface of the cylindrical substrate.

The thin film material includes a plurality of layers. Therefore, different thin film materials can be continuously coated on the surface of the cylindrical substrate, and a thin film material coating can be performed to have a various material compositions and structures.

The thin film material includes a first thin film material and a second thin film material, and the first thin film material and the second thin film material are different from each other. Therefore, the different thin film materials can be continuously coated on the surface of the cylindrical substrate and the thin film material coating can be performed to have a various material compositions and structures.

Another embodiment is a method for coating a thin film in a rolling manner. The method includes: forming a sacrificial layer on a planar substrate; depositing a thin film material on the sacrificial layer; removing the planar substrate and the sacrificial layer; floating the thin film material from which the planar substrate and the sacrificial layer have been removed on a liquefied material; rolling a cylindrical substrate after contacting the cylindrical substrate with the thin film material; coating the thin film material on a surface of the cylindrical substrate during the rolling of the cylindrical substrate; reinforcing the thin film material coated on the surface of the cylindrical substrate; and completing a tubular thin film by removing the cylindrical substrate after reinforcing the thin film material.

The completing a tubular thin film includes removing the cylindrical substrate by contracting the cylindrical substrate or by using an etchant. Therefore, a tubular free-standing thin film structure can be formed, so that it is possible to manufacture a fiber having excellent mechanical, electrical, and thermal characteristics.

Further another embodiment is an apparatus for coating a thin film in a rolling manner. The apparatus includes: a first stage portion to which an end of a cylindrical substrate is fixed and which rolls or moves the cylindrical substrate; a second stage portion to which the other end of the cylindrical substrate is fixed and which is interlocked with the first stage portion thereby rolling or moving the cylindrical substrate; and a base which is disposed under a position corresponding to a target area of the cylindrical substrate. The base includes a liquefied material, and wherein a thin film material floats on the liquefied material.

The first stage portion and the second stage portion move the cylindrical substrate in a direction perpendicular to the ground. Therefore, the cylindrical substrate and the thin film material floating on the liquefied material can precisely come in contact with each other.

Since the target area comes in contact with the thin film material by the moving of the cylindrical substrate, van der Waals force may act between the thin film material and the surface of the cylindrical substrate.

After the target area contacts the thin film material, the first stage portion and the second stage portion roll the cylindrical substrate. Therefore, the thin film material can be coated on the surface of the cylindrical substrate.

Other details of the embodiment of the present invention are included in the detailed description and drawings.

DETAILED DESCRIPTION

The features, advantages and method for accomplishment of the present invention will be more apparent from referring to the following detailed embodiments described as well as the accompanying drawings. However, the present invention is not limited to the embodiment to be disclosed below and is implemented in different and various forms. The embodiments bring about the complete disclosure of the present invention and are only provided to make those skilled in the art fully understand the scope of the present invention. The present invention is just defined by the scope of the appended claims.

While terms such as the first and the second, etc., can be used to describe various components, the components are not limited by the terms mentioned above. The terms are used only for distinguishing between one component and other components. Therefore, the first component to be described below may be the second component within the spirit of the present invention.

Terms used in the present specification are provided for description of only specific embodiments of the present invention, and not intended to be limiting. In the present specification, an expression of a singular form includes the expression of plural form thereof if not specifically stated. The terms "comprises" and/or "comprising" used in the specification is intended to specify characteristics, numbers, steps, operations, components, parts or any combination thereof which are mentioned in the specification, and intended not to exclude the existence or addition of at least one another characteristics, numbers, steps, operations, components, parts or any combination thereof.

Unless differently defined, all terms used herein including technical and scientific terms have the same meaning as commonly understood by one of ordinary skill in the art to which the present invention belongs. Also, commonly used terms defined in the dictionary should not be ideally or excessively construed as long as the terms are not clearly and specifically defined in the present application.

Hereinafter, preferred embodiments in accordance with the present invention will be described with reference to the accompanying drawings. The preferred embodiments are provided so that those skilled in the art can sufficiently understand the present invention, but can be modified in various forms and the scope of the present invention is not limited to the preferred embodiments.

Figure 1:
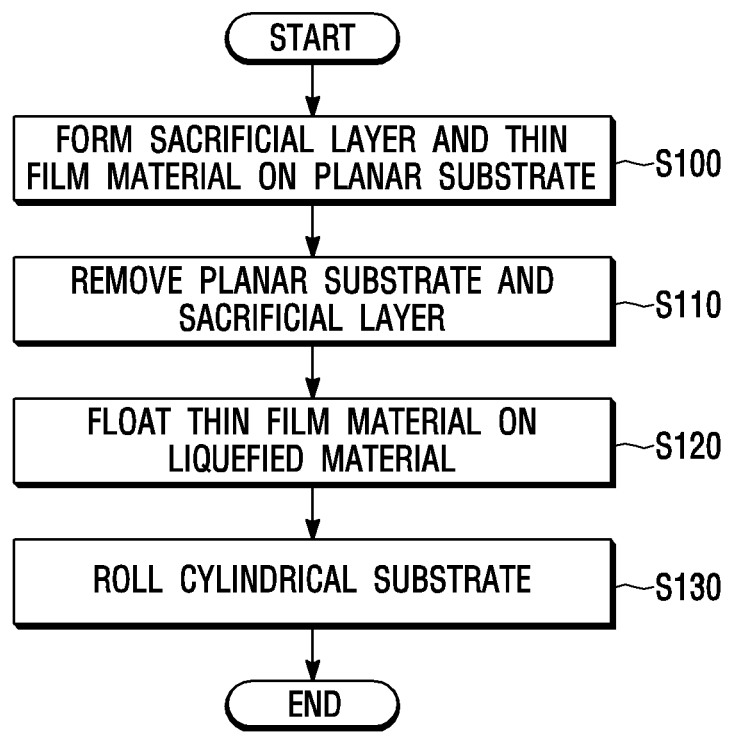
FIG. 1 is a flowchart showing a method for coating a thin film in a rolling manner in accordance with an embodiment of the present invention.
Figure 2A:
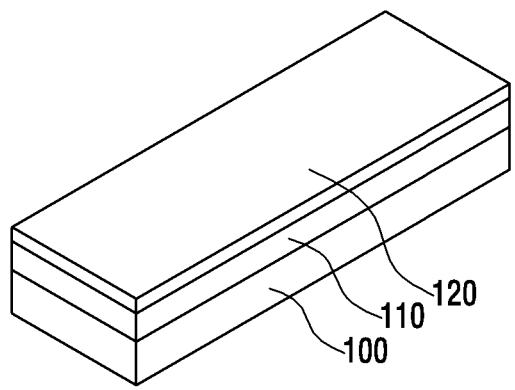
FIGS. 2a to 2d are views showing the method for coating a thin film in a rolling manner in accordance with the embodiment of the present invention.
Figure 2B:
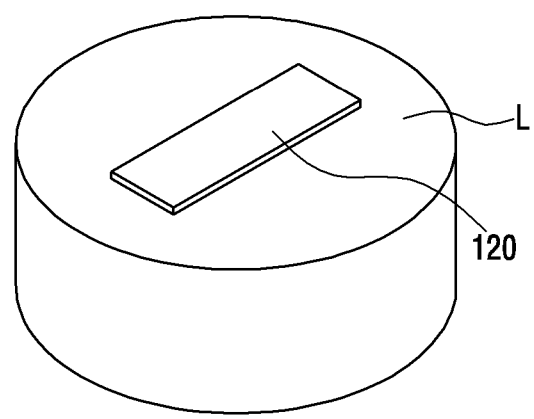
Figure 2C:
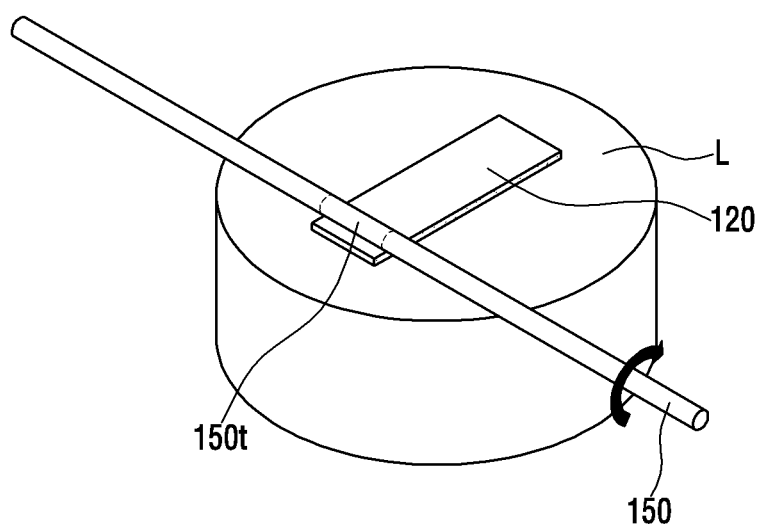
Figure 2D:
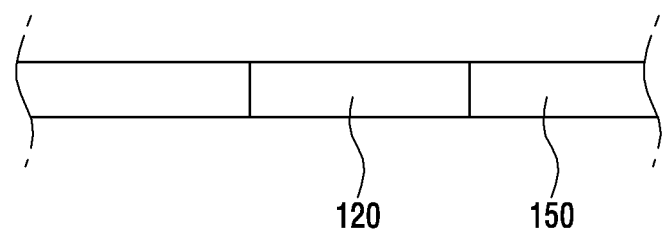
Figure 3:
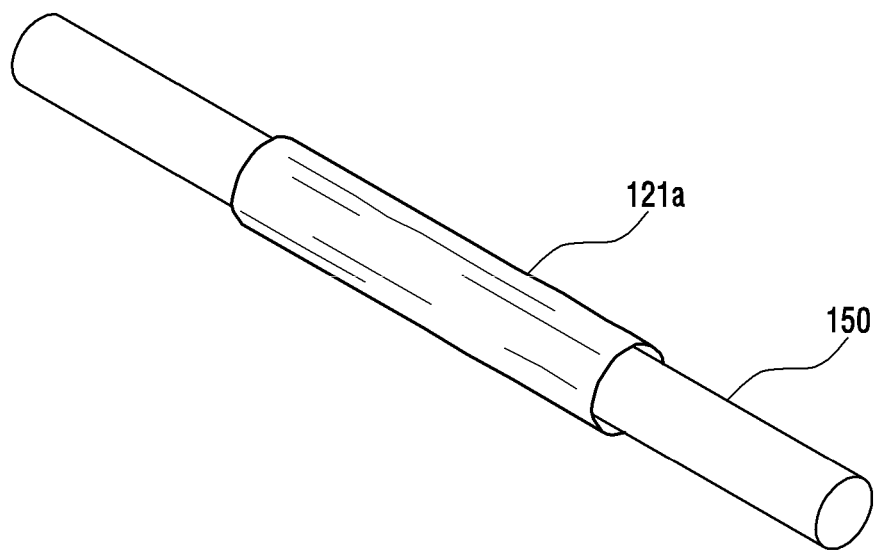
FIG. 3 is a perspective view showing a result product manufactured by the method for coating a thin film in a rolling manner in accordance with the embodiment of the present invention.

FIG. 1 is a flowchart showing a method for coating a thin film in a rolling manner in accordance with an embodiment of the present invention. FIGS. 2a to 2d are views showing the method for coating a thin film in a rolling manner in accordance with the embodiment of the present invention. FIG. 3 is a perspective view showing a result product manufactured by the method for coating a thin film in a rolling manner in accordance with the embodiment of the present invention.

Referring to FIGS. 1 and 2a to 2d, the method for coating a thin film in a rolling manner in accordance with the embodiment of the present invention will be described. First, a sacrificial layer 110 is formed on a planar substrate 100, and then a thin film material 120 is deposited on the sacrificial layer 110 (S100). However, the embodiment of the present invention is not limited to this. According to needs, the thin film material 120 may be directly deposited on the planar substrate 100, or the thin film material 120 may be directly deposited on the sacrificial layer 110, without the planar substrate 100.

The planar substrate 100 may include at least any one selected from the group consisting of polydimethylsiloxane (PDMS), glass, pyrex, silicon, Teflon, polystyrene, polyethylene, lactate, styrene, acrylate, silicone polymer, silicone copolymer, epoxy polymer, epoxy copolymer, acrylic polymer, and acrylic copolymer. The planar substrate 100 may be used to support the sacrificial layer 110 or the thin film material 120. The planar substrate 100 needs to be removed in the subsequent process.

The sacrificial layer 110 may include a material which can be dissolved in an etchant. The sacrificial layer 110 may include, for example, Cu, Ni, etc. The sacrificial layer 110 may have a shape in which it is deposited on the solid planar substrate 100. Alternatively, the sacrificial layer 110 may have a foil shape and may be formed in the form of a thick film capable of maintaining its shape without being supported by the planar substrate 100.

The sacrificial layer 110 may include at least any one selected from the group consisting of polyvinylchloride, neoprene, polyvinylalcohol (PVA), polymethylmetaacrylate (PMMA), polybenzylmetaacrylate (PBMA), polystyiene, polysylene, Spin On Glass (SOG), polydimethylsiloxane (PDMS), polyvinylformal (PVFM), parylene, polyester, epoxy, polyether, and polyimide.

The sacrificial layer 110 may be deposited on the planar substrate 100 by any one of thermal evaporator, CVD, PVD, sputtering or spin coating.

The thin film material 120 may be deposited on the sacrificial layer 110 by any one of thermal evaporator, CVD, PVD, sputtering or spin coating. The thin film material 120 may be formed to have a thickness less than that of the sacrificial layer 110. The thickness at which the thin film material 120 is deposited may be selected by a skilled person in the art if necessary. The thin film material 120 is deposited with a relatively small thickness, so that the thin film material 120 can be easily coated on a target area 150t of a cylindrical substrate 150 in the subsequent process. Herein, the cylindrical substrate 150 is shown in the FIG. 2c. But, the cylindrical substrate 150 is able to be replaced to other shaped substrate. For example, the cylindrical substrate 150 is able to be replaced to tubular substrate or the other shaped substrate through this application. Subsequently, the thin film material 120 is deposited on the planar substrate 100 and on the sacrificial layer 110, and then the planar substrate 100 and the sacrificial layer 110 are removed respectively (S110). The planar substrate 100 may be first removed by peeling off the planar substrate 100 disposed under the sacrificial layer 110, and then the sacrificial layer 110 may be removed by using the etchant.

Alternatively, in a case where the sacrificial layer 110 is thick enough to maintain its shape without the planar substrate 100, the thin film material 120 can be deposited on the sacrificial layer 110 without the planar substrate 100. Therefore, in this case, the sacrificial layer 110 can be removed by immediately floating the sacrificial layer 110 on the etchant.

Subsequently, the thin film material 120 from which the planar substrate 100 and the sacrificial layer 110 have been removed floats on a liquefied material L (S120). The thin film material 120 can float on the liquefied material L by using the surface tension of the liquefied material L. The liquefied material L used herein may be water (H$_2$O). However, the embodiment of the present invention is not limited to this and may include any liquefied material available to a skilled person in the art.

Then, after the thin film material 120 floats on the liquefied material L, the cylindrical substrate 150 is contacted with the thin film material 120. In the state where the surface of the cylindrical substrate 150 is in contact with the thin film material 120, the cylindrical substrate 150 is rolled (S130).

Specifically, after the thin film material 120 is disposed to contact the target area 150t of the cylindrical substrate 150, the cylindrical substrate 150 is rolled and the thin film material 120 is coated on the target area 150t of the cylindrical substrate 150 by van der Waals force between the thin film material 120 and the surface of the cylindrical substrate 150.

Here, the conformal contact between the thin film material 120 and the surface of the cylindrical substrate 150 increases the van der Waals force. When the van der Waals force is greater than the adhesive force between the liquefied material L and the thin film material 120, the coating operation can be performed.

Here, the greater the van der Waals force between the cylindrical substrate 150 and the thin film material 120 is, the more easily the coating operation is performed. The smaller the thickness at which the thin film material 120 is deposited, the less the bending stiffness of the thin film material 120 floating on the liquefied material L is and the greater the van der Waals force is because the conformal contact between the thin film material 120 and the surface of the cylindrical substrate 150 is possible. Therefore, the smaller the thickness at which the thin film material 120 is deposited, the more easily the coating operation is performed.

Referring to FIG. 3, shown is a result product obtained by coating a thin film 121a on the surface of the cylindrical substrate 150 by the method for coating a thin film in a rolling manner in accordance with the embodiment of the present invention.

Figure 4:
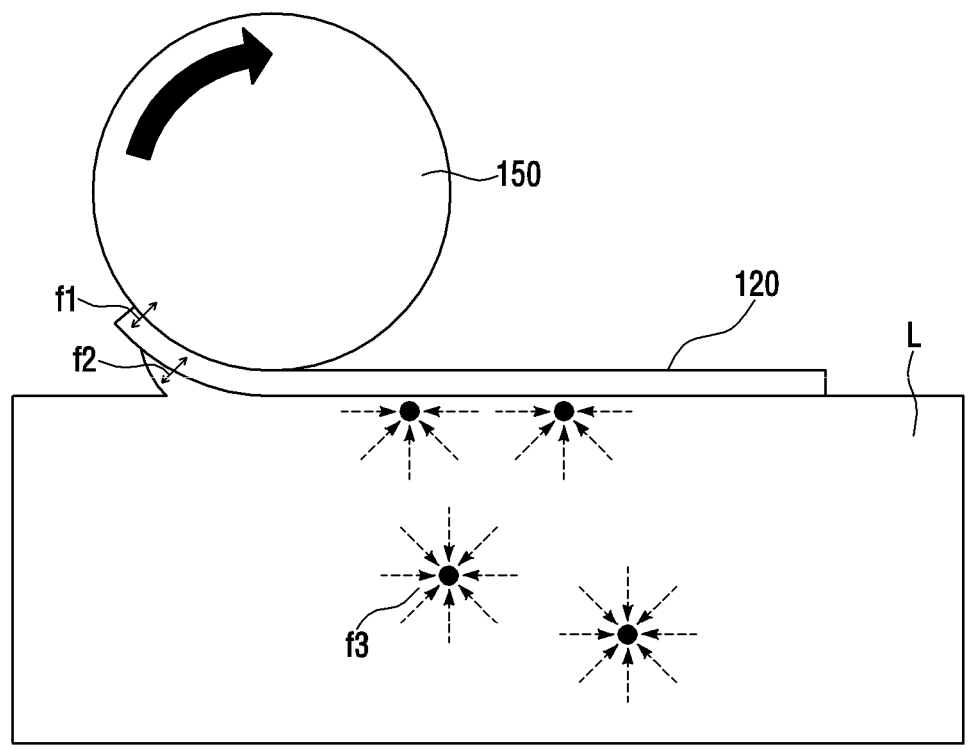
FIG. 4 is a view for describing an operation principle of the method for coating a thin film in a rolling manner in accordance with the embodiment of the present invention.

FIG. 4 is a view for describing an operation principle of the method for coating a thin film in a rolling manner in accordance with the embodiment of the present invention.

Referring to FIG. 4, when the van der Waals force f1 between the cylindrical substrate 150 and the thin film material 120 floating on the liquefied material L is greater than the adhesive force f2 between the liquefied material L and the thin film material 120, the thin film coating operation can be performed. A force f3 by the interaction of the cohesive force between liquid molecules included in the liquefied material L forms a strong surface tension on the surface of the liquefied material L and functions to float the thin film material 120 on the surface of the liquefied material L.

Here, during the process of performing the thin film coating operation, when the thin film material 120 floating on the liquefied material L is coated by rolling the cylindrical substrate 150, the thickness at which the thin film material 120 is coated on the cylindrical substrate 150 can be controlled by controlling the number of times the cylindrical substrate 150 is rolled. Also, the diameter of the thin film material 120 which is coated can be controlled by controlling the diameter of the cylindrical substrate 150.

Figure 5A:
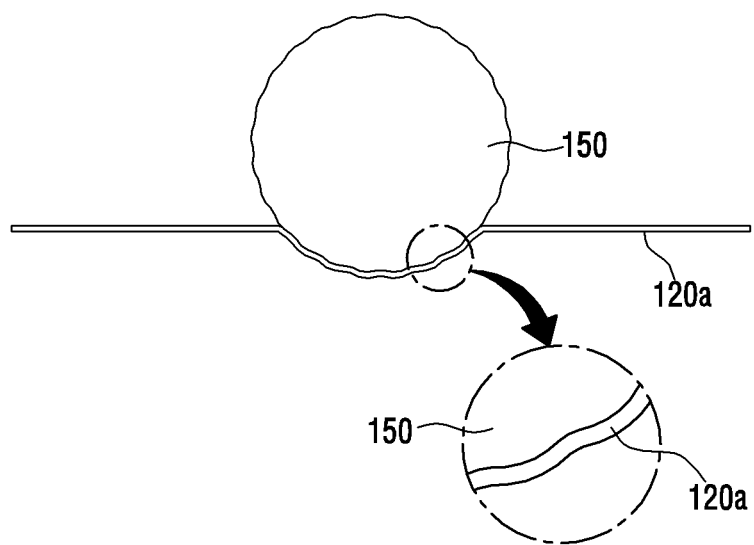
FIGS. 5a and 5b are views for comparing the degrees of thin film coating, depending on the thickness of the thin film material.
Figure 5B:
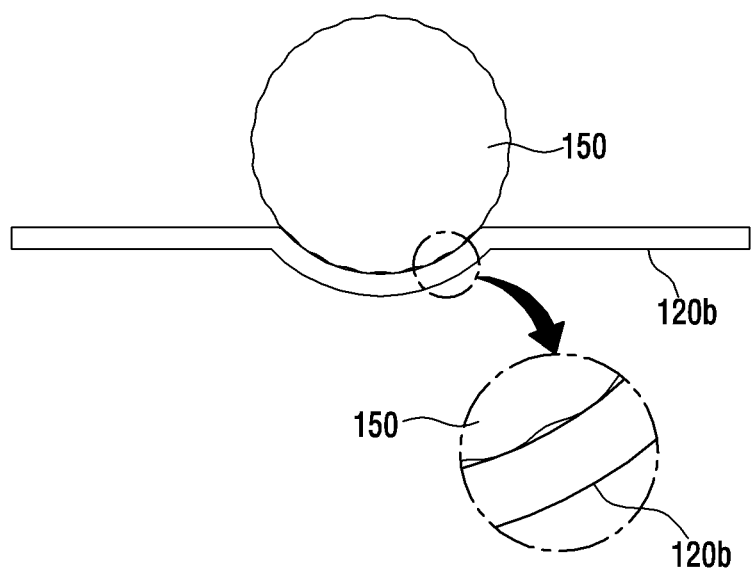

FIGS. 5a and 5b are views for comparing the degrees of thin film coating, depending on the thickness of the thin film material.

Referring to FIG. 5a, when the thickness of a thin film material 120a is relatively small, the bending stiffness of the thin film material 120a floating on the liquefied material L is low and the conformal contact between the thin film material 120a and the surface of the cylindrical substrate 150 is possible. Therefore, it can be seen that the van der Waals force between the thin film material 120a and the surface of the cylindrical substrate 150 is strong. Here, the conformal contact means a structure in which the thin film material 120a is coated along the entire rugged surface of the cylindrical substrate 150 while contacting. Also, the conformal contact means a state of increasing the surface contact area.

Referring to FIG. 5b, when the thickness of a thin film material 120b is relatively large, the bending stiffness of the thin film material 120b floating on the liquefied material L is high and the conformal contact between the thin film material 120b and the rough surface of the cylindrical substrate 150 is difficult. Therefore, it can be seen that the van der Waals force between the thin film material 120b and the surface of the cylindrical substrate 150 is weak. Therefore, the smaller the thickness at which the thin film material 120b is deposited, the greater the adhesive force between the thin film material 120b and the cylindrical substrate 150 is and the more easily the coating operation is performed.

Figure 6:
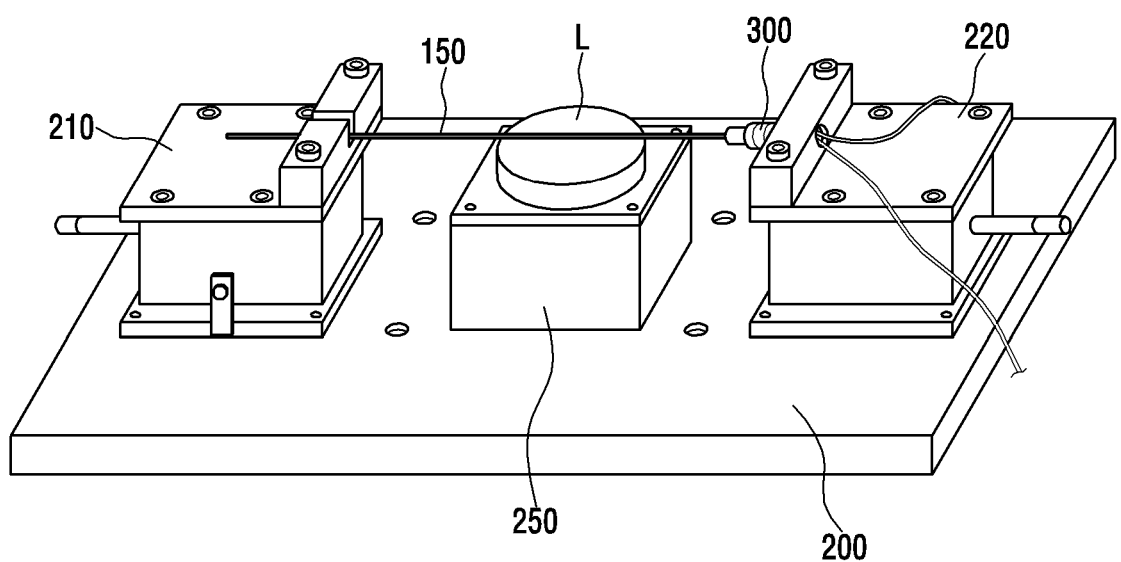
FIG. 6 is a schematic view showing a thin film coating apparatus using the rolling manner in accordance with the embodiment of the present invention.

FIG. 6 is a schematic view showing a thin film coating apparatus using the rolling manner in accordance with the embodiment of the present invention.

Referring to FIG. 6, shown is an embodiment of an apparatus for implementing the above-described method for coating a thin film in a rolling manner. However, the thin film coating apparatus using the rolling manner is not limited to this. It is clear that the apparatus can be modified within a range that a skilled person in the art can understand.

The thin film coating apparatus using the rolling manner in accordance with the embodiment of the present invention includes a support stage 200, a first stage portion 210, a second stage portion 220, a base 250, a drive motor 300, or the like.

The first stage portion 210 and the second stage portion 220 may be fixed on the support stage 200. An end of the cylindrical substrate 150 is fixed to the first stage portion 210. The first stage portion 210 rolls the cylindrical substrate 150 or moves the cylindrical substrate 150 in a direction perpendicular to the ground. However, the embodiment of the present invention is not limited to this. The first stage portion 210 may move the cylindrical substrate 150 in a direction parallel with the ground.

The other end of the cylindrical substrate 150 is fixed to the second stage portion 220. The second stage portion 220 is interlocked with the first stage portion 210, thereby rolling the cylindrical substrate 150 or moving the cylindrical substrate 150 in a direction perpendicular to the ground. Likewise, the embodiment of the present invention is not limited to this. The second stage portion 220 may move the cylindrical substrate 150 in a direction parallel with the ground.

The drive motor 300 is installed on any one or both of the first stage portion 210 and the second stage portion 220 and may function to roll the cylindrical substrate 150. Although FIG. 6 shows that the drive motor 300 is installed on the second stage portion 220, the embodiment of the present invention is not limited to this.

The base 250 may be disposed under a position corresponding to the target area 150*t* of the cylindrical substrate 150 which is fixed by the first stage portion 210 and the second stage portion 220. The base 250 includes the liquefied material L. The thin film material 120 floats on the liquefied material L, and the thin film material 120 comes in contact with the target area 150*t* of the cylindrical substrate 150, and then, the cylindrical substrate 150 comes to roll, so that the thin film material 120 is coated on the target area 150*t* of the cylindrical substrate 150.

Figure 7:
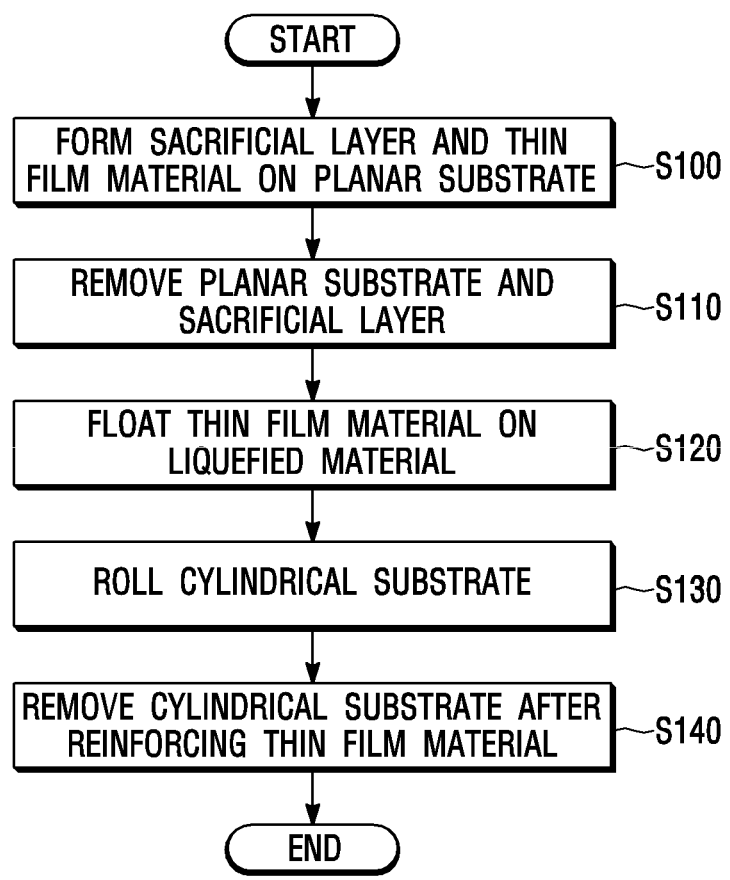
FIG. 7 is a flowchart showing a method for coating a thin film in a rolling manner in accordance with another embodiment of the present invention.
Figure 8:
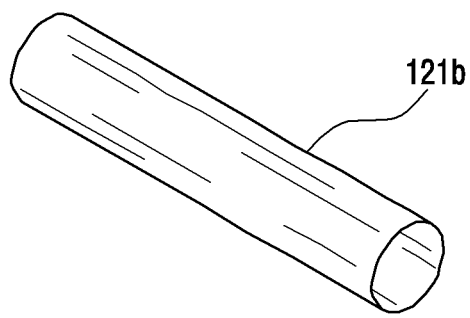
FIG. 8 is a view showing an example in which a tubular thin film has been implemented by the method for coating a thin film in a rolling manner in accordance with the embodiment of the present invention.

FIG. 7 is a flowchart showing a method for coating a thin film in a rolling manner in accordance with another embodiment of the present invention. FIG. 8 is a view showing an example in which a tubular thin film has been implemented by the method for coating a thin film in a rolling manner in accordance with the embodiment of the present invention.

Referring to FIG. 7, the method for coating a thin film in a rolling manner in accordance with the embodiment of the present invention will be described. First, the sacrificial layer 110 is formed on the planar substrate 100, and then the thin film material 120 is deposited on the sacrificial layer 110 (S100). The planar substrate 100 and the sacrificial layer 110 are removed respectively (S110). The thin film material 120 from which the planar substrate 100 and the sacrificial layer 110 have been removed floats on the liquefied material L (S120). In the state where the surface of the cylindrical substrate 150 is in contact with the thin film material 120, the cylindrical substrate 150 is rolled (S130). The thin film coating operation is performed on the surface of the cylindrical substrate 150, and the coated thin film is reinforced, and then the inner cylindrical substrate 150 can be removed from the reinforced thin film (S140).

As a result, a tubular thin film 121*b* may be formed by removing the cylindrical substrate 150 from the coated thin film (see FIG. 8). Here, the cylindrical substrate 150 can be removed from the coated thin film by contracting the cylindrical substrate 150 or by using the etchant.

Through the reinforcing of the thin film, the thickness of the thin film to be coated can be increased by increasing the number of times the cylindrical substrate 150 is rolled, and the tubular thin film 121*b* having a sufficient rigidity can be formed due to the increase of the thickness of the coated thin film. Alternatively, the coated thin film can be reinforced by performing a physical treatment or chemical treatment on the coated thin film in the cylindrical substrate 150.

Referring to FIG. 8, after the thin film material 120 is coated on the target area 150*t* of the cylindrical substrate 150, the coated thin film material 120 is reinforced and the inner cylindrical substrate 150 is removed from the reinforced thin film, so that the tubular thin film 121*b* is formed. In the case where the thin film coated on the cylindrical substrate 150 has a sufficient rigidity, when the cylindrical substrate 150 is removed, the tubular thin film 121*b* can be formed without the substrate.

The tubular thin film 121*b* can be used according to needs in the manufacture of various electronic products by a skilled person in the art.

Figure 9A:
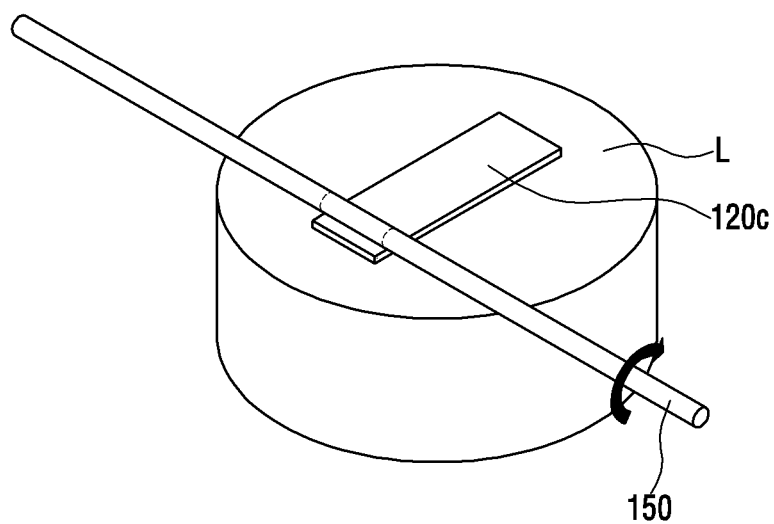
FIGS. 9a to 9c are views showing the method for coating a thin film in a rolling manner in accordance with further another embodiment of the present invention.
Figure 9B:
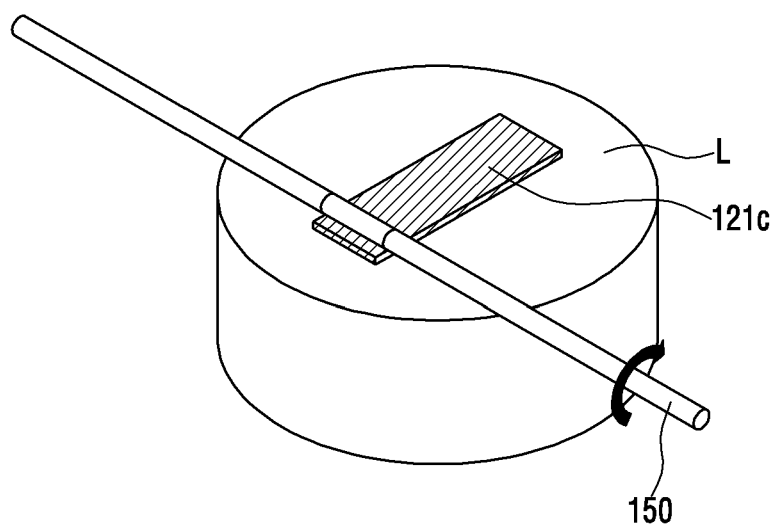
Figure 9C:
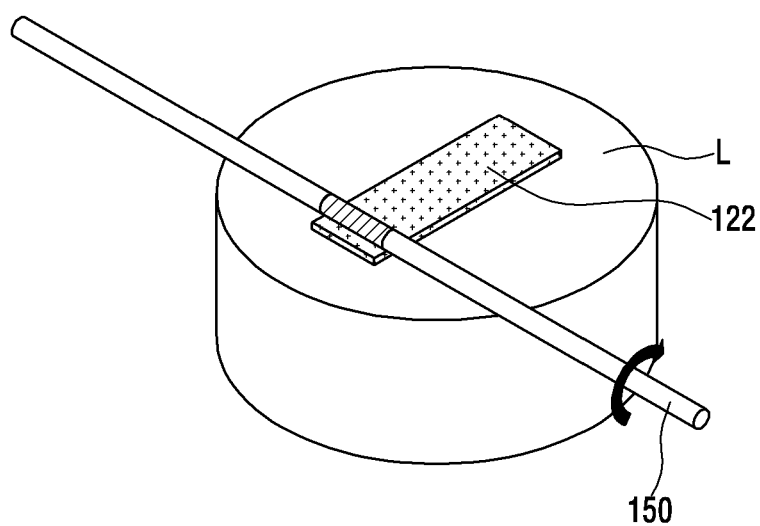
Figure 10:
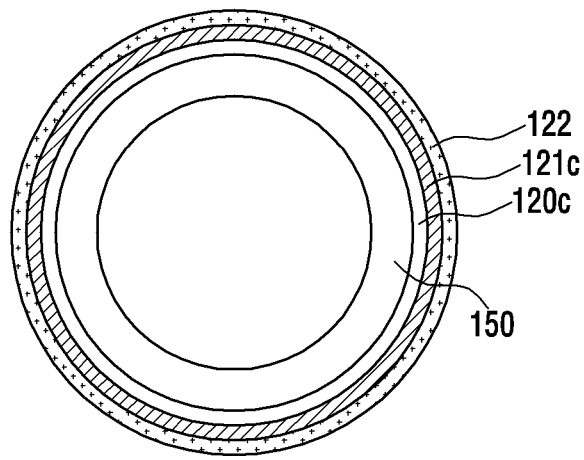
FIG. 10 is a cross sectional view of a thin film having a multi-layered structure which has been by the method for coating a thin film in a rolling manner in accordance with the embodiment of the present invention.

FIGS. 9*a* to 9*c* are views showing the method for coating a thin film in a rolling manner in accordance with further another embodiment of the present invention. FIG. 10 is a cross sectional view of a thin film having a multi-layered structure which has been by the method for coating a thin film in a rolling manner in accordance with the embodiment of the present invention.

Referring to FIGS. 9*a* to 9*c* and 10, in the method for coating a thin film in a rolling manner in accordance with the embodiment of the present invention, a thin film including a plurality of layers may be formed.

For example, the thin film having a multi-layer structure may include a first layer 120*c*, a second layer 121*c*, and a third layer 122. However, the embodiment of the present invention is not limited to this. The thin film may include a larger or smaller number of the layers.

Here, the method for forming each of the first layer 120*c*, the second layer 121*c*, and the third layer 122 is substantially the same as the above-described method for coating a thin film in a rolling manner.

The first layer 120*c* is coated on the target area 150*t* of the cylindrical substrate 150 and the second layer 121*c* is coated on the first layer 120*c*, and then the third layer 122 is coated on the second layer 121*c*. As a result, the thin film having a multi-layer structure shown in FIG. 10 may be formed.

Here, the first layer 120*c*, the second layer 121*c*, and the third layer 122 may include different materials respectively.

By using the method for coating a thin film in a rolling manner in accordance with the embodiment of the present invention, it is possible to manufacture the thin film having a specific multi-layer structure, which cannot be manufactured by existing methods, by easily changing the specimens of the material and structure of the thin film.

By using the method for coating a thin film in a rolling manner in accordance with the embodiments of the present invention, a very thin film can be transferred to or coated on the cylindrical substrate or curved substrate, so that the embodiment of the present invention can be used in the manufacture of various electronic products.

For example, the embodiment of the present invention can be used in the manufacture of the electrode of a steerable catheter, bio-monitoring, bio-integrated device, etc. Also, the embodiment of the present invention can be used in the manufacture of products for observing the inside of human body and the inside of a small hole.

In the past, a planar polymer substrate has been mainly used in the manufacturing process of stretchable electronics. However, a metal thin film is coated on a polymer tube, etc., by using the method for coating a thin film in a rolling manner in accordance with the embodiments of the present invention and the thin film coating apparatus, the method and the apparatus according to the embodiment of the present invention can be developed as one field of next generation stretchable electronics with a 3-dimensional structure that is different from the structure of the planar substrate. Also, a composite of an insulating material and a conductive material is coated, so that the method and the apparatus according to the embodiment of the present invention can be used in the manufacture of an energy storage device such as a super-capacity, etc.

Also, according to the method for coating a thin film in a rolling manner in accordance with the embodiments of the present invention and the thin film coating apparatus, the thin film is transferred to the cylindrical substrate and then the cylindrical substrate (or a core) is removed, so that the tubular thin film can be formed. By using the tubular thin film, thin film products having excellent mechanical and electrical characteristics such as strength, toughness, elongation, electrical conductivity, etc., can be implemented and applied to various fields including wearable electronics, fiber, or the like.

Besides, according to the embodiment of the present invention, synergies beyond expectation can be obtained in a variety of industries through multi-scale materials because the thin film having a nano-scale thickness is made into a macro-scale fiber.

Hereinafter, industries to which the method for coating a thin film in a rolling manner in accordance with the embodiments of the present invention and the thin film coating apparatus can be applied will be described.

In the manufacture of the electrode of a steerable catheter, through use of the spirit of the present invention, it is possible to coat a very thin film on the polymer tube. Also, it is possible to form an electrode which does not peel off regardless of the expansion of the tube within a blood vessel, thereby improving the mechanical reliability.

A super-capacitor with very thin laminated films can be manufactured by forming and coating the insulating material and the conductive material in the form of a bi-layer. The thus coated and manufactured capacitor has very high storage efficiency compared to an existing planar capacitor.

The tubular thin film can be manufactured by transferring the thin film to the cylindrical substrate and removing the cylindrical substrate. The tubular thin film manufactured in this manner has a lamination structure formed by very thin films. The tubular thin film can be manufactured with a variety of composites. The tubular thin film may have excellent strength, fracture toughness, elongation, electrical and thermal characteristics, etc.

By coating the thin film on human tissue having a cylindrical shape such as hair, blood vessels, tendons, etc., the method and the apparatus according to the embodiment of the present invention can be used for bio-monitoring or used to manufacture a bio-integrated device, etc. Through this, it is possible to easily obtain a variety of information on health status such as a body temperature, etc., and to apply the method and the apparatus according to the embodiment to a healthcare system.

The method and the apparatus according to the embodiment of the present invention can be used to manufacture a steerable camera for observing the inside of which the entrance is a small hole, for example, the inside of human body.

The planar polymer substrate has been mainly used in the manufacturing process of the existing electronics. However, the metal thin film is easily coated on the polymer tube, etc., so that it is possible to implement next generation electronics that is difficult to implement on the planar substrate, such as wearable electronics with a 3-dimentional structure, flexible electronics, stretchable electronics, or the like.

The method for coating a thin film in a rolling manner in accordance with the embodiment of the present invention can be applied not only to the above examples but also to various fields and can be easily utilized. Therefore, there is a high possibility that the method is applied and developed in new markets as well as existing markets.

While the embodiment of the present invention has been described with reference to the accompanying drawings, it can be understood by those skilled in the art that the present invention can be embodied in other specific forms without departing from its spirit or essential characteristics. Therefore, the foregoing embodiments and advantages are merely exemplary and are not to be construed as limiting the present invention. The present teaching can be readily applied to other types of apparatuses. The description of the foregoing embodiments is intended to be illustrative, and not to limit the scope of the claims.

What is claimed is:

1. A method for coating a thin film in a rolling manner, the method comprising:
    removing a sacrificial layer after depositing a thin film material on the sacrificial layer;
    floating the thin film material from which the sacrificial layer has been removed on a liquefied material;
    rolling a cylindrical substrate after contacting the cylindrical substrate with the thin film material; and
    coating the thin film material on a surface of the cylindrical substrate by using an attraction force between the surface of the cylindrical substrate and the thin film material.

2. The method of claim 1, wherein the attraction force is greater than an adhesive force between the liquefied material and the thin film material.

3. The method of claim 1, wherein the sacrificial layer comprises at least one of Cu and Ni.

4. The method of claim 3, wherein, in the removing, the sacrificial layer is removed by using an etchant.

5. The method of claim 1, wherein the thin film material comprises a plurality of layers.

6. The method of claim 5, wherein the thin film material comprises a first thin film material and a second thin film material, and wherein the first thin film material and the second thin film material are different from each other.

7. A method for coating a thin film in a rolling manner, the method comprising:
    forming a sacrificial layer on a planar substrate;
    depositing a thin film material on the sacrificial layer;
    removing the planar substrate and the sacrificial layer;
    floating the thin film material from which the planar substrate and the sacrificial layer have been removed on a liquefied material;
    rolling a cylindrical substrate after contacting the cylindrical substrate with the thin film material;

coating the thin film material on a surface of the cylindrical substrate during the rolling of the cylindrical substrate;

reinforcing the thin film material coated on the surface of the cylindrical substrate; and completing a tubular thin film by removing the cylindrical substrate after reinforcing the thin film material.

8. The method of claim 7, wherein the completing a tubular thin film comprises removing the cylindrical substrate by contracting the cylindrical substrate or by using an etchant.

\* \* \* \* \*